United States Patent [19]

Feringa et al.

[11] Patent Number: 5,580,485
[45] Date of Patent: Dec. 3, 1996

[54] BLEACH ACTIVATION

[75] Inventors: Ben L. Feringa; Marcel Lubben, both of Groningen; Roelant M. Hermant, Leiden; Robin S. Twisker, Rotterdam, all of Netherlands; Lawrence Que, Jr., Roseville, Minn.

[73] Assignee: Lever Brothers Company, Division of Conopco, Inc., New York, N.Y.

[21] Appl. No.: 451,346

[22] Filed: May 26, 1995

[30] Foreign Application Priority Data

Jun. 13, 1994 [EP] European Pat. Off. .............. 94201680

[51] Int. Cl.$^6$ ................ C11D 3/26; C11D 3/28; C11D 3/395; C11D 7/38
[52] U.S. Cl. ............... 510/311; 252/186.42; 252/186.43
[58] Field of Search .......................... 252/102, 186.42, 252/186.43

[56] References Cited

U.S. PATENT DOCUMENTS

| | | | |
|---|---|---|---|
| 3,532,634 | 10/1970 | Woods | 252/95 |
| 3,644,455 | 2/1972 | Onsager | 260/439 R |
| 4,119,557 | 10/1978 | Postlewaite | 252/99 |
| 4,169,092 | 9/1979 | Bayer | 546/10 |
| 4,728,455 | 3/1988 | Rerek | 252/99 |
| 5,077,394 | 12/1991 | Dolphin et al. | 530/505 |
| 5,246,621 | 9/1993 | Favre et al. | 252/186.33 |

FOREIGN PATENT DOCUMENTS

| | | |
|---|---|---|
| 0528228 | 2/1993 | European Pat. Off. . |
| 0537381 | 4/1993 | European Pat. Off. . |
| 544490 | 6/1993 | European Pat. Off. . |
| 0553607 | 8/1993 | European Pat. Off. . |

*Primary Examiner*—Paul Lieberman
*Assistant Examiner*—Gregory R. Delcotto
*Attorney, Agent, or Firm*—Milton L. Honig

[57] ABSTRACT

A bleach and oxidation catalyst is provided comprising a catalytically active iron complex which can activate hydrogen peroxide or peroxy acids and was found to have both favourable stain removal and remarkable dye transfer inhibition properties. In addition, a considerably improved stability of these compounds in alkaline aqueous environment has been obtained, in particular at the peroxy compound concentrations generally present in the fabric washing liquor.

7 Claims, No Drawings

BLEACH ACTIVATION

FIELD OF THE INVENTION

The invention relates to activation of bleaches employing peroxy compounds including hydrogen peroxide or hydrogen peroxide adducts, which liberate hydrogen peroxide in aqueous solution, and peroxy acids; to compounds that activate or catalyse peroxy compounds; to bleach compositions, including detergent bleach compositions, which contain a catalyst for peroxy compounds; and to processes for bleaching and/or washing substrates using the aforementioned types of compositions.

In particular, the present invention is concerned with the novel use of iron compounds as catalysts for the bleach activation of peroxy compounds.

BACKGROUND OF THE INVENTION

Peroxide bleaching agents for the use in laundring have been known for many years. Such agents are effective in removing stains, such as tea, fruit, and wine stains, from clothing at or near boiling temperatures. The efficacy of peroxide bleaching agents drop off sharply at temperatures below 60° C.

Previous patent applications dealt with environmentally acceptable manganese ions and complexes. U.S. Pat. No. 4,728,455 discusses the use of Mn(III)-gluconate as peroxide bleach catalyst with high hydrolytic and oxidative stability; relatively high ratios of ligand (gluconate) to Mn are, however, needed to obtain the desired catalytic system. Moreover, the performance of these Mn-based catalysts is inadequate when used for bleaching in the low-temperature region of about 20°–40° C., and they are restricted in their efficacy to remove a wide range of stains.

In several patent documents, for instance EP-A-458,379, novel triazacyclononane-based manganese complexes are disclosed, which display a high catalytic oxidation activity at low temperatures, which is particularly suitable for bleaching purposes. A major improvement of the bleaching activity could be obtained by the fact that these compounds are stable under washing conditions, e.g. high alkalinity and oxidizing environment (as a result of the presence of hydrogen peroxide or peroxy acids).

In addition to the above-mentioned stain removal, dye transfer is a well-known problem in the art and has been addressed in various ways. For instance, an improved dye transfer inhibition has been obtained by using Fe-porphyrin and Fe-phtalocyanine complexes (see EP-A-537,381, EP-A-553,607, EP-A-538,228).

It is well known that the stability of Fe-co-ordination complexes in alkaline aqueous media in the presence of peroxide compounds is very poor; in EP-A-537,381 and EP-A-553,607, methods are disclosed for improvement in this respect.

This poor stability of Fe-co-ordination species has resulted in the necessity of very low concentrations of peroxide and, additionally, the use of polymers (see EP-A-538,228). These measures, however, only reduce the negative effects of the above-indicated poor stability to some extent and do not provide a complete solution for this problem.

We have now surprisingly found catalytically highly active iron compounds which can activate hydrogen peroxide or peroxy acids, thereby providing both favourable stain removal, remarkable dye transfer inhibition properties, and, alternatively, oxidation of organic substrates such as olefins, alcohols and unactivated hydrocarbons.

In addition, a considerably improved stability of these compounds in alkaline aqueous environment has been obtained, in particular at the peroxy compound concentrations generally present in the wash liquor during the fabric washing cycle.

SUMMARY OF THE INVENTION

In one aspect, the present invention provides a bleach and oxidation catalyst comprising an Fe-complex having formula A $$[LFeX_n]^z Y_q \tag{A}$$

or precursors thereof, in which

Fe is iron in the II, III, IV or V oxidation state;

X represents a coordinating species such as $H_2O$, ROH, $NR_3$, RCN, $OH^-$, $OOH^-$, $RS^-$, $RO^-$, $RCOO^-$, $OCN^-$, $SCN^-$, $N_3^-$, $CN^{13}$ , $F^-$, $Cl^-$, $Br^-$, $I^-$, $O^{2-}$, $NO_3^-$, $NO_2^-$, $SO_4^{2-}$, $SO_3^{2-}$, $PO_4^{3-}$ or aromatic N donors such as pyridines, pyrazines, pyrazoles, imidazoles, benzimidazoles, pyrimidines, triazoles and thiazoles with R being H, optionally substituted alkyl, optionally substituted aryl;

n is an integer number ranging from 0–3;

Y is a counter ion, the type of which is dependent on the charge of the complex; q=z/[charge Y];

z denotes the charge of the complex and is an integer which can be positive, zero or negative; if z is positive, Y is an anion such as $F^-$, $Cl^-$, $Br^-$, $I^-$, $NO_3^-$, $BPh_4^-$, $ClO_4^{1313}$, $BF_4^-$, $PF_6^-$, $RSO_3^4$, $RSO_4^-$, $SO_4^{2-}$, $CF_3SO_3^-$, $RCOO^-$ etc; if z is negative, Y is a common cation such as an alkali metal, alkaline earth metal or (alkyl)ammonium cation etc;

L represents a ligand which is an organic molecule containing a number of hetero atoms, e.g. N, P, O, S etc. which co-ordinates via all or some of its hetero atoms and/or carbon atoms to the iron centre. In another aspect, the present invention provides a bleaching composition comprising a peroxy compound bleach preferably selected from hydrogen peroxide, hydrogen peroxide- liberating or -generating compounds, peroxyacids and their salts, peroxyacid bleach precursors, and mixtures thereof, and a catalyst according to the present invention.

DETAILED DESCRIPTION OF THE INVENTION

Generally, the Fe-complex catalyst of the invention may be used in a bleaching system comprising a peroxy compound or a precursor thereof and suitable for use in the washing and bleaching of substrates including laundry, dishwashing and hard surface cleaning. Alternatively, the Fe-complex catalyst of the invention may also be used in the textile, paper and woodpulp industries.

As already stated, an advantage of the Fe-complex catalysts according to the present invention is that they exhibit both a high oxidation activity and a remarkably high stability in alkaline aqueous media in the presence of peroxy compounds.

A second advantage of the Fe-complex catalysts of the invention is that their optimal bleaching activity is observed at lower pH values than those observed for the triazacyclononane-based manganese complex compounds mentioned above. This advantage may turn out to be very beneficial in view of the current tendency to shift the pH during fabric washing from highly alkaline (typically, a pH of 10) to more neutral values.

An additional advantage is that such compounds are active as dye-transfer inhibition agents as shown in Example 3. Another advantage is that the catalysts of the invention have a relatively low molecular weight and are, consequently, very weight-effective. Furthermore, they can be easily prepared.

Precursors of the active Fe-complex catalysts of the invention can be any iron co-ordination complex, which, under fabric washing conditions, is transformed into the active iron complex of general formula A. Alternatively, the precursor of the Fe-complex of the invention can be a mixture of an iron salt, such as $Fe(NO_3)_3$, and the ligand L (see Example 2).

A preferred class of ligands is that of pentadentate ligands, which co-ordinate via five hetero atoms, such as nitrogen, oxygen and sulphur atoms, to the Fe atom. These hetero atoms are preferably nitrogen atoms. The nitrogen atoms can be part of tertiary, secondary or primary amine groups, tertiary, secondary or primary amide groups, or part of heterocyclic aromatic ring systems, e.g. pyridines, pyrazines, pyrazoles, imidazoles, benzimidazoles, thiazoles, triazoles and pyrimidines, or combinations thereof.

Examples of preferred ligands in their simplest forms are:

(i) pyridin-2-yl-methyl containing ligands such as: N,N-bis(pyridin-2-yl-methyl)-bis(pyridin-2-yl)methylamine; N,N-bis(pyrazol-1-yl-methyl)-bis(pyridin-2-yl )methylamine; N,N-bis(imidazol-2-yl-methyl)-bis(pyridin-2-yl) methylamine; N,N-bis(1,2,4-triazol-1-yl-methyl)-bis(pyridin-2-yl) methylamine; N,N-bis(pyridin-2-yl-methyl)-bis(pyrazol-l-yl) methylamine; N,N-bis(pyridin-2-yl-methyl)-bis(imidazol-2-yl) methylamine; N,N-bis(pyridin-2-yl-methyl)-bis(1,2,4-triazol-l-yl) methylamine;

(ii) 2-amino-ethyl containing ligands such as: N,N-bis(2-amino-ethyl)-bis(pyridin-2-yl) methylamine; N,N-bis(2 -amino-ethyl)-bis(pyrazol-1-yl) methylamine; N,N-bis(2-amino-ethyl)-bis( imidazol-2-yl ) methylamine; N,N-bis(2-amino-ethyl)-bis(1,2,4 -triazol-l-yl) methylamine; N, N-bis(pyridin-2 -yl-methyl)-bis(2-amino-ethyl) methylamine; N, N-bis(pyrazol-1-yl-methyl)-bis(2-amino-ethyl) methylamine; N,N-bis(imidazol-2-yl-methyl)-bis(2-amino-ethyl) methylamine; N,N-bis(1,2,4 -triazol-1-yl-methyl)-bis(2-amino-ethyl) methylamine;

The most preferred ligand is: N,N-bis(pyridin-2-yl-methyl)-bis(pyridin-2-yl)methylamine, hereafter referred to as $N_4Py$.

Suitable counter ions are those which give rise to the formation of storage-stable solids. Combination of the preferred iron complexes with the counter ion Y preferably involves counter ions such as $RCOO^-$, $BPh_4^-$, $ClO_4^-$, $BF_4^-$, $PF_6^-$, $RSO_3^-$, $RSO_4^-$, $SO_4^{2-}$, $NO_3^-$, wherein R=H, optionally substituted phenyl, naphtyl or $C_1$–$C_4$ alkyl. Preferred coordinating species X are $CH_3CN$, $H_2O$, $Cl^-$, $OH^-$, and $OOH^-$.

The effective level of the Fe-complex catalyst, expressed in terms of parts per million (ppm) of iron in an aqueous bleaching solution, will normally range from 0.001 ppm to 100 ppm, preferably from 0.01 ppm to 20 ppm, most preferably from 0.1 ppm to 10 ppm. Higher levels may be desired and applied in industrial bleaching processes, such as textile and paper pulp bleaching. The lower range levels are preferably used in domestic laundry operations.

THE DETERGENT BLEACH COMPOSITION

The bleaching composition of the invention has particular application in detergent formulations to form a new and improved detergent bleach composition within the purview of the invention, comprising a peroxy compound bleach-as defined above, the aforesaid Fe-complex catalyst having general formula (A), a surface-active material and a detergency builder.

The Fe-complex catalyst will be present in the detergent bleach composition of the invention in amounts so as to provide the required level in the wash liquor. Generally, the Fe-complex catalyst level in the detergent bleach composition corresponds to an iron content of from 0.0005% to 0.5% by weight. When the dosage of detergent bleach composition is relatively low, e.g. about 1–2 g/l, the Fe content in the formulation is suitably 0.0025 to 0.5%, preferably 0.005 to 0.25% by weight. At higher product dosages, as used e.g. by European consumers, the Fe-content in the formulation is suitably 0.0005 to 0.1%, preferably 0.001 to 0.05% by weight.

Detergent bleach compositions of the invention are effective over a wide pH-range of between 7 and 13, with optimal pH-range lying between 8 and 11.

THE PEROXY BLEACHING COMPOUND

The peroxy bleaching compound may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 5–35% by weight, preferably from 1–25% by weight.

Another suitable hydrogen peroxide generating system is a combination of a $C_1$–$C_4$ alkanol oxidase and a $C_1$–$C_4$ alkanol, especially a combination of methanol oxidase (MOX) and ethanol (see Example 3). Such combinations are disclosed in International Application PCT/EP 94/03003 (Unilever), which is incorporated herein by reference.

Alkylhydroxy peroxides are another class of peroxy bleaching compounds. Examples of these materials include cumene hydroperoxide and t-butyl hydroperoxide.

Organic peroxyacids may also be suitable as the peroxy bleaching compound. Such materials normally have the general formula:

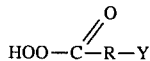

wherein R is an alkylene or substituted alkylene group containing from 1 to about 20 carbon atoms, optionally having an internal amide linkage; or a pheylene or substituted phenylene group; and Y is hydrogen, halogen, alkyl, aryl, an imido-aromatic or non-aromatic group, a COOH or

group or a quaternary ammonium group.

Typical monoperoxy acids useful herein include, for example:

(i) peroxybenzoic acid and ring-substituted peroxybenzoic acids, e.g. peroxy-α-naphthoic acid;

(ii) aliphatic, substituted aliphatic and arylalkyl monoperoxyacids, e.g. peroxylauric acid, peroxystearic acid and N,N-phthaloylaminoperoxy caproic acid (PAP); and (iii) 6-octylamino-6-oxo-peroxyhexanoic acid.

Typical diperoxyacids useful herein include, for example:

(iv) 1,12-diperoxydodecanedioic acid (DPDA);

(v) 1,9-diperoxyazelaic acid;

(vi) diperoxybrassilic acid; diperoxysebasic acid and diperoxyisophthalic acid;

(vii) 2-decyldiperoxybutane-1,4-diotic acid; and (viii) 4,4'-sulphonylbisperoxybenzoic acid.

Also inorganic peroxyacid compounds are suitable, such as for example potassium monopersulphate (MPS). If organic or inorganic peroxyacids are used as the peroxygen compound, the amount thereof will normally be within the range of about 2–10% by weight, preferably from 4–8% by weight.

All these peroxy compounds may be utilized alone or in conjunction with a peroxyacid bleach precursor and/or an organic bleach catalyst not containing a transition metal. Generally, the bleaching composition of the invention can be suitably formulated to contain from 2 to 35%, preferably from 5 to 25% by weight, of the peroxy bleaching agent.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412, 934 and 4,675,393.

Another useful class of peroxyacid bleach precursors is that of the cationic i.e. quaternary ammonium substituted peroxyacid precursors as disclosed in US Pat. Nos. 4,751, 015 and 4,397,757, in EP-A0284292 and EP-A-331,229. Examples of peroxyacid bleach precursors of this class are:

2-(N,N,N-trimethyl ammonium) ethyl sodium-4-sulphonphenyl carbonate chloride - (SPCC);

N-octyl,N,N-dimehyl-$N_{10}$-carbophenoxy decyl ammonium chloride - (ODC);

3-(N,N,N-trimethyl ammonium) propyl sodium-4-sulphophenyl carboxylate; and

N,N,N-trimethyl ammonium toluyloxy benzene sulphonate.

A further special class of bleach precursors is formed by the cationic nitriles as disclosed in EP-A-303,520 and in European Patent Specification No.'s 458,396 and 464,880.

Any one of these peroxyacid bleach precursors can be used in the present invention, though some may be more preferred than others.

Of the above classes of bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of said preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoloxy benzoate; SPCC; trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

The precursors may be used in an amount of up to 12%, preferably from 2–10% by weight, of the composition.

As an alternative to the above described peroxide generating systems, molecular oxygen may be used as the oxidant.

THE SURFACE-ACTIVE MATERIAL

The detergent bleach composition according to the present invention generally contains a surface-active material in an amount of from 10 to 50% by weight. Said surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents" Volumes I and II, by Schwartz, Perry and Berch.

Typical synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{10}$) benzene sulphonates, particularly sodium linear secondary alkyl ($C_{10}$–$C_{15}$) benzene sulphonates; sodium alkyl glyceryl ether sulphates, especially those ester of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by racting alpha-olefins ($C_8$–$C_{20}$) with sodium bisulphite and those derived by reaction paraffins with $SO_2$ and $C_{12}$ and then hydrolysing with a base to produce a random sulphonate; sodium an ammonium $C_7$–$C_{12}$ dialkyl sulphosccinates; and olefin sulphonates which term is used to describe material made by reacting olefins, particularly $C_{10}$–$C_{20}$ alpha-olefins, with $SO_3$ and then neutralising and hydroysing the reaction product. The preferred anionic detergent compounds are sodium ($C_{10}$–$C_{15}$) alkylbenzene sulphonates, sodium $C_{16}$–$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, longchain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As disclosed by EP-A-544,490, the performance of the hereinbefore described bleach catalyst, may be dependent upon the active detergent system and the builder system present in the detergent bleach composition of the invention.

The detergent bleach composition of the invention will preferably comprise from 1–15% wt of anionic surfactant and from 10–40% by weight of nonionic surfactant. In a further preferred embodiment the detergent active system is free from $C_{16}$–$C_{12}$ fatty acids soaps.

THE DETERGENCY BUILDER

The composition of the invention normally and preferably also contains a detergency builder in an amount of from about 5–80% by weight, preferably from about 10–60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144, 226 and 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also know as Zeolite P), zeolite C, zeolite X, zeolite Y and also the zeolite P type as described in EP-A-0384070.

In particular, the compositions of the inventionsray contain any one of the organic and inorganic builder materials, though, for environmental reasons, phosphate builders are preferably omitted or only used in very small amounts.

Typical builders usable in the present invention are, for example, sodium carbonate, calcite/carbonate, the sodium salt of nitrilotriacetic acid, sodium citrate, carboxymethyloxy malonate, carboxymethyloxy succinate and the water-insoluble crystalline or amorphous aluminosilicate builder material, each of which can be used as the main builder, either alone or in admixture with minor amounts of other builders or polymers as co-builder.

It is preferred that the composition contains not more than 5% by weight of a carbonate builder, expressed as sodium carbonate, more preferable not more than 2.5% by weight to substantially nil, if the composition pH lies in the lower alkaline region of up to 10.

OTHER INGREDIENTS

Apart form the components already mentioned, the detergent bleach composition of the invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilizers, such as phosphonic acid derivatives (i.e. Dequest® types); fabric softening agents; inorganic salts and alkaline buffering agents, such as sodium sulphate, sodium silicate etc.; and usually in very small amounts, fluorescent agents; perfumes; enzymes, such as proteases, cellulases, lipases, amylases and oxidases; germicides and colourants.

When using a hydrogenperoxide source, such as sodium perborate or sodium percarbonate, as the bleaching compound, it is preferred that the composition contains not more than 5% by weight of a carbonate buffer, expressed as sodium carbonate, more preferable not more than 2.5% by weight to substantially nil, if the composition pH lies in the lower alkaline region of up to 10.

Of the additives, transition metal sequestrants, such as EDTA and the phosphonic acid derivatives, e.g. ethylene diamine tetra-(methylene phosphonate)-EDTMP- are of special importance, as not only do they improve the stability of the catalyst/$H_2O_2$ system and sensitive ingredients, such as enzymes, fluorescent agents, perfumes and the like, but also improve the bleach performance, especially at the higher pH region of above 10, particularly at pH 10.5 and above.

The invention will now be further illustrated by way of the following non-limiting Examples.

EXAMPLE 1

Preparation of [Fe($N_4$Py) ($CH_3$CN)]($ClO_4$)$_2$.2 $H_2O$ (FeL$_1$).

The ligand $N_4$Py was prepared as follows:

To pyridyl ketone oxime (3 g, 15.1 mmol) was added ethanol (15 ml), concentrated ammonia solution (15 mL) and $NH_4$OAc (1.21 g, 15.8 mmol). The solution was warmed until reflux. To this solution was added 4.64 g Zn in small portions. After the addition of all Zn, the mixture was refluxed for 1 h. and allowed to cool to ambient temperature. The solution was filtered and water (15 ml) was added. Solid NaOH was added until PH>>10 and the solution was extracted with $CH_2Cl_2$ (3×20 ml). The organic layers were dried over $Na_2SO_4$ and evaporated until dryness. Bis(pyridin-2-yl)methylamine (2.39 g, 12.9 mmol) was obtained as a colourless oil in 86% yield, showing the following analytical characteristics:

$^1$H NMR (360 MHz, CDCl$_3$): δ2.64 (s, 2H, NH$_2$), 5.18 (s, 1H, CH), 6.93 (m, 2H, pyridine), 7.22 (m, 2H, pyridine), 7.41 (m, 2H, pyridine), 8.32 (m, 2H, pyridine); $^{13}$C NMR (CDCl$_3$): δ62.19 (CH), 121.73 (CH), 122.01 (CH), 136.56 (CH), 149.03 (CH), 162.64 (Cq).

To picolylchloride hydrochloride (4.06 g, 24.8 mmol) was added, at 0° C., 4.9 ml of a 5N NaOH solution. This emulsion was added by means of a syringe to bis(pyridin-2-yl)methylamine (2.3 g, 12.4 mmol) at 0° C. Another 5 ml of a 5N NaOH solution was added to this mixture. After warming to ambient temperature, the mixture was stirred vigorously for 40 hrs. The mixture was put in an ice bath and HClO$_4$ was added until pH<1, whereupon a brown solid precipitated. The brown precipitate was collected by filtration and recrystallized from water. While stirring, this mixture was allowed to cool to ambient temperature, whereupon a light-brown solid precipitated which was collected by filtration and washed with cold water and air-dried (1.47 g). The free amine could be obtained by precipitating the salt with 2N NaOH and extraction with $CH_2Cl_2$. The free amine should be stored under an atmosphere of argon because it is sensitive to $CO_2$.

The ligand N4Py showed the following characteristics:

$^1$H NMR (360 MHz, CDCl$_3$): δ3.96 (s, 4H, CH$_2$), 5.34 (s, 1H, CH), 7.00–7.10 (m, 4H, pyridine), 7.52–7.64 (m, 8H, pyridine), 8.44–8.53 (m, 4H, pyridine);

$^{13}$C NMR (CDCl$_3$): δ57.36 (CH2), 72.06 (CH), 121.90 (CH), 122.18 (CH), 123.01 (CH), 124.09 (CH), 136.35

(CH), 136.46 (CH), 149.06 (CH), 149.33 (CH), 159.83 (Cq), 160.00 (Cq).

Subsequently, $[(N_4Py)Fe(CH_3CN)](ClO_4)_2 \cdot 2\ H_2O$ was prepared as follows:

To a solution of 0.144 g (0.392 mmol) of $N_4Py$ in methanol/acetonitrile (2 ml/2 ml) was added 0.215 g (0.403 mmol) $Fe(ClO_4)_3 \cdot 10\ H_2O$. After stirring for 5 minutes, the solution was placed in an ethyl acetate bath. The crystals formed overnight, were collected and washed with ethyl acetate to yield 0.178 grams of $[(N_4Py)Fe(CH_3CN)](ClO_4)_2 \cdot 2\ H_2O$ as dark red crystals (yield: 65%).

$^1H$ NMR (360 MHz, $CD_3CN$): δ4.27 (d, 2H, J=18.1 Hz), 4.40 (d, 2H, J=18.1 Hz), 6.34 (s, 1H); 7.06 (d, 2H, J=7.8 Hz), 7.33 (m, 4H), 7.68 (m, 2H), 7.88 (m, 4H), 8.90 (d, 2H, J=5.4 Hz), 9.03 (d, 2H, J=5.4 Hz)

UV-vis (acetone) $[\lambda_{max}$, nm ($\epsilon$, $M^{-1}cm^{-1}$)]: 382 (5650), 458 (3970)

Anal.Calcd for $C_{25}H_{28}Cl_2FeN_6O_1$: C,42.94; H, 4.04; N, 12.02.

Found: C, 43.21; H, 3.76; N, 12.02.

In the Examples 2, 3 and 4, the above-described complex $[(N_4Py)Fe(CH_3CN)](ClO_4)_2 \cdot 2\ H_2O$ is referred to as $Fe(N_4Py)$.

EXAMPLE 2

The bleaching activity of the Fe-catalyst prepared according to Example 1 was demonstrated in the presence hydrogen peroxide on standard tea-stained (BC-1) cotton test cloths.

The experiments were carried out at 40° C. and at a pH of 6 and 8 in a temperature-controlled glass beaker equipped with a magnetic stirrer, thermocouple and a pH electrode.

Two pieces of test cloth were stirred for 60 minutes in 1 liter of a $8.6 \times 10^{-3}$ mol/l hydrogen peroxide solution in millipore water, containing concentrations of the compounds as indicated in Table 1. After rinsing with demineralised water, the test cloths were dried for 7 minutes in a microwave oven. The reflectance ($R_{460}*$) of the test cloths was measured on a Macbeth 1500/plus colour measuring system including UV-filter before and after treatment. The difference ($\Delta R_{460}*$) between both reflectance values thus obtained gives a measure of the bleaching performance, i.e. higher $\Delta R_{460}*$ values correspond to an improved bleaching performance.

TABLE 1

|  | conc. (mol/l) | $\Delta R_{460}*$ (at pH = 6) | $\Delta R_{460}*$ (at pH = 8) |
| --- | --- | --- | --- |
| blank | — | 4.4 | 4.4 |
| $Fe(NO_3)_3$ | $5 \times 10^{-6}$ | 3.2 | 4.6 |
| $Fe(N_4Py)$ | $5 \times 10^{-6}$ | 7.9 | 12.4 |
| $Fe(NO_3)_3$ + $N_4Py$ | $5 \times 10^{-6}$(Fe) + $10 \times 10^{-6}(N_4Py)$ | — | 7.5 |

In Table 1, $Fe(N_4Py)$ refers to the Fe-catalyst prepared according to Example 1. The blank and $Fe(NO_3)_3$ experiment were used as control. As observed in Table 1, no experiment has been carried out at pH=6 for $Fe(NO_3)_3+N_4Py$.

These measurements show that improved bleaching performance is obtained when $Fe(N_4Py)$ or a combination of Fe and the ligand $N_4Py$ are present in solution.

EXAMPLE 3

The bleaching activity of the Fe catalyst, prepared according to example 1, was demonstrated in the presence of the hydrogen peroxide generating enzyme Methanol Oxidase (MOX) and ethanol on standard tea stained (BC-1) cotton test cloths.

The experiments were carried out in a phosphate buffer (pH=8) at 40° C. in a temperature controlled glass beaker equipped with a magnetic stirrer, thermocouple and a pH electrode.

Two pieces of test cloth were vigorously shaken for 6 hours in 0.25 liter of an oxygen saturated phosphate bufer at pH=8 (millipore water), containing 200 mg MOX, 20 mM ethanol and concentrations of the compounds as indicated in Table 2. As described in example 2, higher $\Delta R_{460}*$, values correspond to an improved bleaching performance.

TABLE 2

|  | conc. (mol/l) | $\Delta R_{460}*$ |
| --- | --- | --- |
| blank | — | 7.2 |
| $Fe(NO_3)_3$ | $1 \times 10^{-5}$ | 6.8 |
| $Fe(N_4Py)$ | $1 \times 10^{-5}$ | 10.8 |

In Table 2, $Fe(N_4Py)$ refers to the Fe catalyst, prepared according to example 1. The blanc and $Fe(NO_3)_3$ experiment were used as control.

These measurements show that improved bleaching performance is obtained when $Fe(N_4Py)$ is present in solution.

EXAMPLE 4

The dye oxidation activity of the Fe-catalyst prepared according to Example 1 was demonstrated in the presence peracetic acid on a dye known as acid red 88.

The experiments were carried out at ambient temperature at pH=8 in a 1 cm cuvet in the presence of $2.2 \times 10^{-3}$ mol/l peracetic acid and $2 \times 10^{-4}$ mol/l acid red 88. The absorbance at 503 nm ($A_{503}$), which is the maximum of the characteristic visible absorption of the dye in aqueous media, was measured at t=0 and t=15 minutes. The ratio ($\Delta A_{503}=A_{503}$(t=15)/$A_{503}$(t=0 min)) of the absorbance at t=15 minutes and t=0 gives a measure of the dye-oxidation performance, i.e. an improved dye-oxidation performance results in reduced $\Delta A_{503}$ values.

TABLE 3

|  | conc. (mol/l) | $\Delta A_{503}$ |
| --- | --- | --- |
| blank | — | 1.00 |
| $Fe(NO_3)_3$ | $5 \times 10^{-6}$ | 0.98 |
| $Fe(N_4Py)$ | $5 \times 10^{-6}$ | 0.075 |

$Fe(N_4Py)$ in Table 2 refers to the Fe-catalyst prepared according to Example 1. The blank and $Fe(NO_3)_3$ experiment were used as controls.

These measurements show that improved dye oxidation performance is obtained when $Fe(N_4Py)$ is present in solution.

EXAMPLE 5

The organic substrate oxidation activity of the Fe catalyst, prepared according to example 1, was demonstrated in the presence of hydrogen peroxide on a range of organic substrates.

The experiments were carried out at ambient temperature in acetone. The concentration of the Fe catalyst was $3.5 \times 10^{-6}$ M and the ratio catalyst/$H_2O_2$/substrate was 1/100/860.

The turnover numbers indicated in Table 4 represent the number of molecules formed per molecule of the catalyst as determined after the indicated time of reaction by using gas chromatography. In a blank experiment or in the presence of Fe(NO$_3$)$_3$, essentially no oxidation products could be detected.

TABLE 4

| substrate | product (turnover number) | reaction time |
| --- | --- | --- |
| cyclohexene | 2-cyclohexen-1-ol (18) | 30 minutes |
| | 2-cyclohexen-1-one (9) | |
| | cyclohene epoxide (2) | |
| cyclohexane | cyclohexanol (13) | 30 minutes |
| | cyclohexanon (5) | |
| benzylalcohol | benzylaldehyde (38) | 30 minutes |
| styrene | benzylaldehyde (23) | 30 minutes |
| adamantane | 1-adamantanol (7) | 60 minutes |
| | 2-adamantanol (7) | |
| | 2-adamantanone (4) | |

We claim:

1. A bleaching composition comprising:
   (i) from 2 to 35% by weight of a peroxy bleaching compound; and
   (ii) a catalyst present in an amount to deliver an iron content of from 0.0005 to 0.5% by weight, the catalyst being an Fe-complex having formula (A):

[LFeX$_n$]$^z$Y$_q$  (A)

or precursors thereof, in which

Fe is iron in an oxidation state selected from the group consisting of II, III, IV and V;

X represents a co-ordinating species selected from the group consisting of H$_2$O, ROH, NR$_3$, RCN, OH$^-$, OOH$^-$, RS$^-$, RO$^-$, RCOO$^-$, OCN$^-$, SCN$^-$, N$_3^-$, CN$^-$, F$^-$, Cl$^-$, Br$^-$, I$^-$, O$^{2-}$, NO$_3^{13}$, SO$_4^{2-}$, SO$_3^{2-}$, PO$_4^{3-}$ and aromatic N donors, the donors being selected from the group consisting of pyridines, pyrazines, pyrazoles, imidazoles, benzimidazoles, pyrimidines, triazoles and thiazoles, with R being selected from the group consisting of hydrogen, optionally substituted alkyl and optionally substituted aryl;

n is an integer number ranging from 0–3;

Y is a counter ion, the type of which is dependent on the charge of the complex;

z denotes the charge of the complex and is an integer which can be positive, zero or negative; if z is positive, Y is an anion selected from the group consisting of F$^-$, Cl$^-$, Br$^-$, I$^-$, NO$_3^-$, BPh$_4^-$, ClO$_4^-$, BF$_4^-$, PF$_4^-$, RSO$_3^-$, RSO$_4^-$, SO$_4^{2-}$, CF$_3$SO$_3^-$, RCOO$^-$ and if z is negative, Y is a common cation selected from the group consisting of alkali metal, alkaline earth metal and ammonium cation;

q=z/[charge Y];

L represents a pentadentate ligand having a structural fragment selected from the group consisting of pyridin-2-yl-methyl and 2-amino-ethyl.

2. A composition according to claim 10 wherein the ligand L is N,N-bis(pyridin-2-yl-methyl)-bis(pyridin-2-yl)methylamine.

3. Composition according to claim 1 wherein the ligand L is selected from the group consisting of: N,N-bis(pyridin-2-yl-methyl)-bis(pyridin-2-yl)methylamine; N,N-bis(pyrazol-1-yl-methyl)-bis(pyridin-2-yl)methylamine; N,N-bis(imidazol-2-yl-methyl)-bis(pyridin-2-yl)methylamine; N,N-bis(1,2,4-triazol-1-yl-methyl)-bis(pyridin-2-yl) methylamine; N,N-bis(pyridin-2-yl-methyl)-bis(pyrazol-1-yl)methylamine; N,N-bis(pyridin-2-yl-methyl)-bis(imidazol-2-yl) methylamine; N,N-bis(pyridin-2-yl-methyl)bis(1,2,4-triazol-1-yl) methylamine; N,N-bis(2-amino-ethyl)-bis(pyridin-2-yl)methylamine; N,N-bis(2-amino-ethyl)-bis(pyrazol-1-yl)methylamine; N,N-bis(2-amino-ethyl)-bis(imidazol-2-yl)methylamine; N,N-bis(2-amino-ethyl)-bis(1,2,4-triazol-1-yl) methylamine; N,N-bis(pyridin-2-yl-methyl)-bis(2-amino-ethyl)methylamine; N,N-bis(pyrazol-1-yl-methyl)-bis(2-amino-ethyl N,N-bis(imidazol-2-yl-methyl)bis(2-amino-ethyl)methylamine; and N,N-bis(1,2,4-triazol-1-yl-methyl)-bis(2-aminoethyl)methylamine.

4. Catalyst according to claim 1, wherein X represents a co-ordinating species selected from CH$_3$CN, H$_2$O, Cl$^-$, OH$^-$, and OOH$^-$.

5. Catalyst according to claim 1, wherein the counter ion Y is selected from RCOO$^-$, BPh$_4^-$, ClO$_4^-$, BF$_4^-$, PF$_6^-$, RSO$_3^{13}$, RSO$_4^-$, SO$_4^{2-}$, NO$_3^-$, wherein R=H, optionally substituted phenyl, naphtyl or C$_1$–C$_4$ alkyl.

6. Composition according to claim 1, wherein the peroxy bleaching compound is selected from the group consisting of hydrogen peroxide, hydrogen peroxide- liberating or -generating compounds, peroxyacids and their salts, peroxyacid bleach precursors, and mixtures thereof.

7. Composition according to claim 1, which further comprises a surface-active material, in an amount of from 10 to 50% by weight, and a detergency builder in an amount of from 5 to 80% by weight.

* * * * *